United States Patent [19]
Dobson

[11] Patent Number: 5,407,212
[45] Date of Patent: Apr. 18, 1995

[54] FALLING CARD GAME APPARATUS

[75] Inventor: Michael J. Dobson, Mississauga, Canada

[73] Assignee: Bob's Space Racers, Inc., Daytona Beach, Fla.

[21] Appl. No.: 321,910

[22] Filed: Oct. 12, 1994

[51] Int. Cl.⁶ ............................ A63F 7/02; A61B 5/16
[52] U.S. Cl. ..................................................... 273/446
[58] Field of Search ................. 273/445, 446; 434/236, 434/238, 258

[56] References Cited

U.S. PATENT DOCUMENTS

| | | |
|---|---|---|
| 854,951 | 5/1907 | Kistler . |
| 1,730,726 | 10/1929 | Goerke ............................ 273/446 X |
| 2,834,597 | 5/1958 | Ylinen ................................ 273/446 |
| 3,545,749 | 12/1970 | Schmued .......................... 273/446 |
| 3,717,347 | 2/1973 | Hottendorf ....................... 273/446 |
| 3,747,589 | 7/1973 | Harrison et al. ................. 128/744 |

Primary Examiner—Paul E. Shapiro
Attorney, Agent, or Firm—James E. Larson

[57] ABSTRACT

A game for testing reflex and reaction times in people is provided. The game has a vertical housing mounted to a planar base. The vertical housing defines a channel enclosing a pair of shafts. A card is provided to move along a first shaft and a lifter is provided to move along a second shaft. The lifter engages the card and sets it in an upper limit. A solenoid keeps the card at its upper limit. A start button enables the solenoid to release the card permitting downward movement of the card. A pair of finger grabbers inserted through side walls of the housing enable a player to grab the falling card. Prize lines on a front surface of the card determine if a player has won a prize. A cheat detection system is additionally provided to prohibit a player from grabbing the card before it has initiated downward movement.

19 Claims, 8 Drawing Sheets

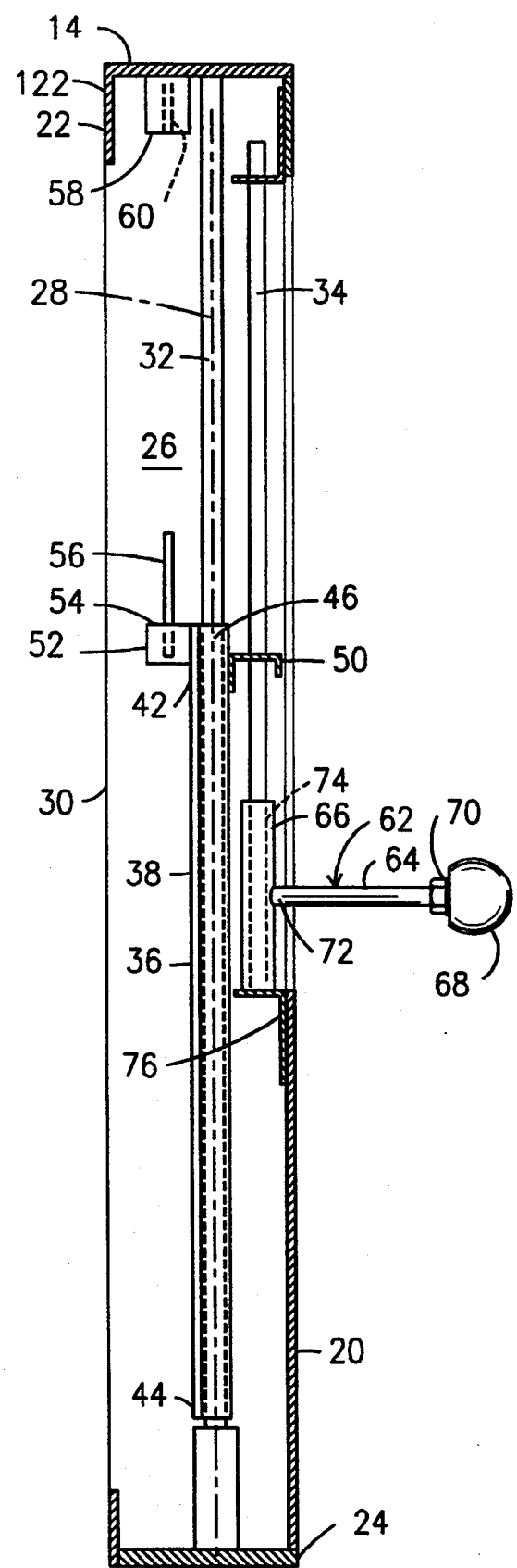
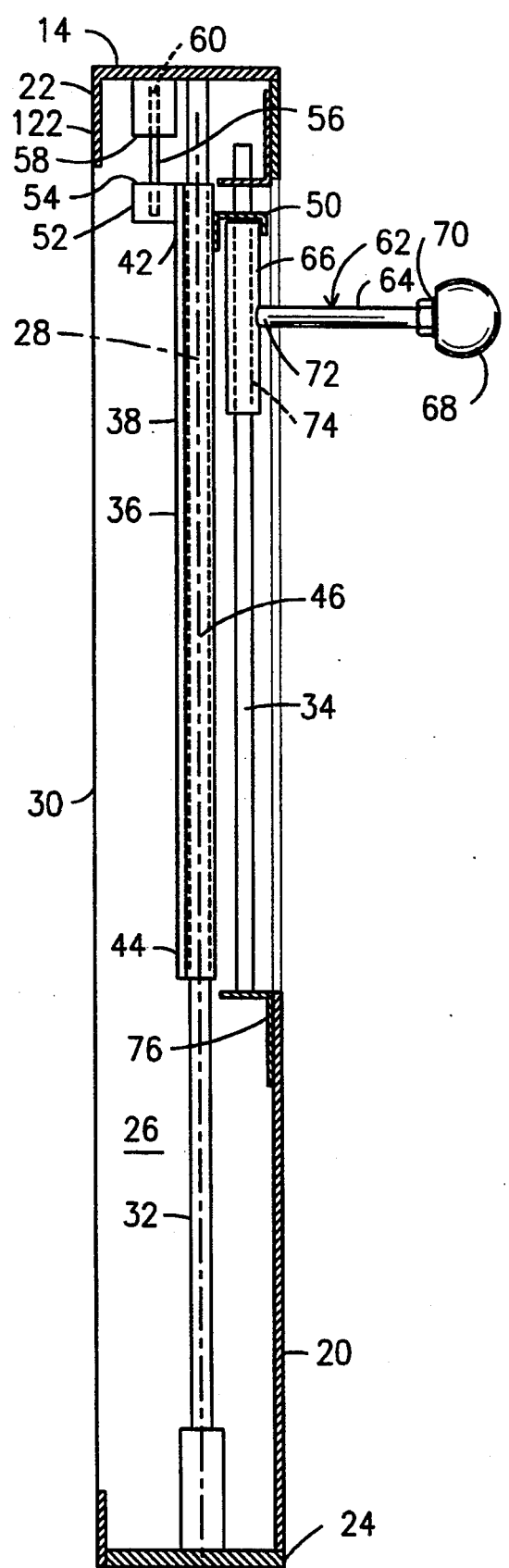

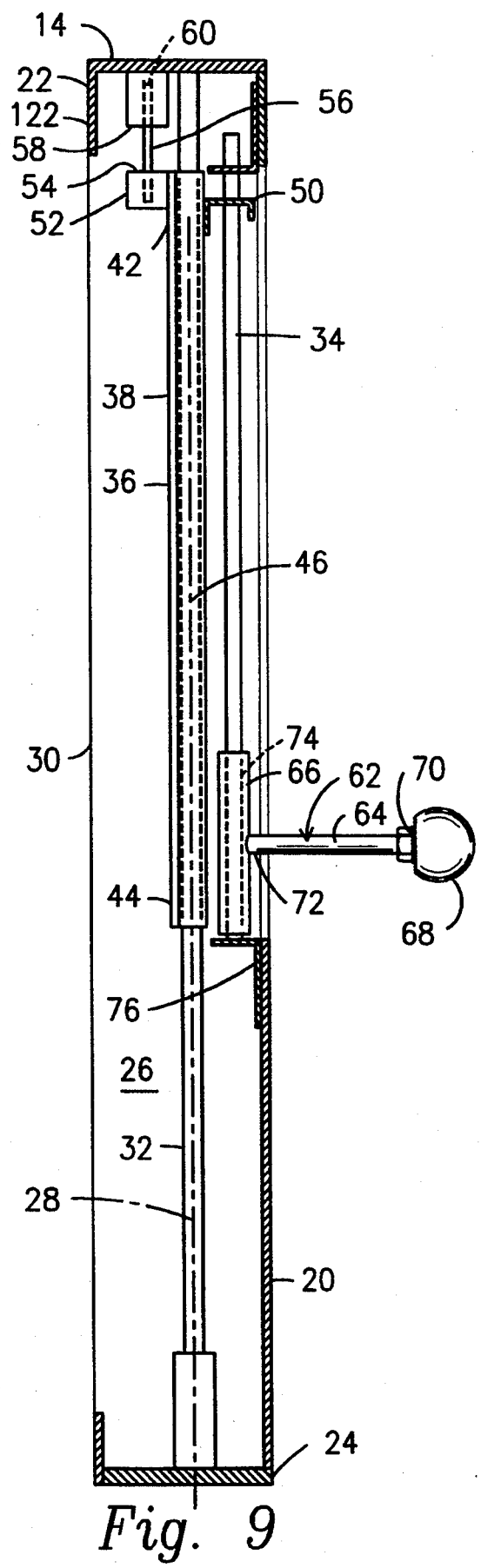
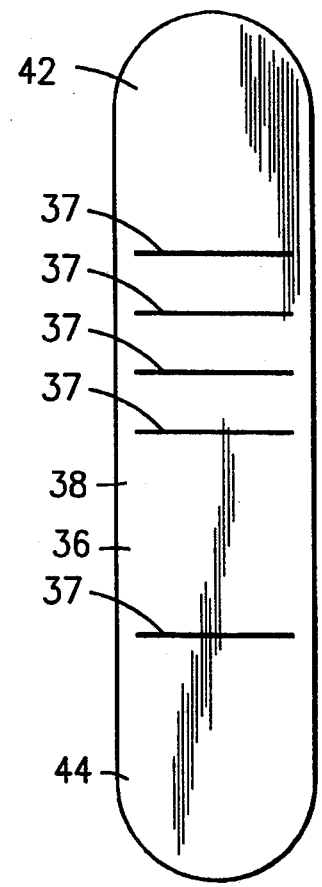
Fig. 9
Fig. 10

FALLING CARD GAME APPARATUS

BACKGROUND OF THE INVENTION

1. Field of the Invention

This invention relates to games for testing reflex and reaction times of people. More particularly, it relates to a game apparatus for testing eye, ear, and hand coordination by having a game player attempt to grab a falling card along a vertical axis after a random time sequence has ended.

2. Description of Prior Art

Amusement parks and arcades have supplied games for testing reflex and reaction times of people for many years. These games have come in a variety of shapes, sizes, and more importantly have tested the reflex and reaction times of people in a large variety of manners.

Some of the games that are known in the prior art for testing reflex and reaction times of people are seen in U.S. Pat. Nos. 854,951, 1,730,726, 2,834,597, 3,545,749, 3,717,347, and 3,747,589. U.S. Pat. No. 854,951 describes a means for catching a projectile at a plurality of elevations as the projectile moves upward. The projectile is caught by a retaining catch bar having an engaging edge with a longitudinal series of rachet catching teeth which are inclined in a direction permitting the free upward travel of the projectile. U.S. Pat. No. 1,730,726 describes a game having a perforated ball or projectile located on a guide rod. Semi-circular cuts or incisions intercept and hold the ball at various elevations as the ball ascends the guide rod. U.S. Pat. No. 2,834,597 describes a reaction time meter with a channel for a falling body. When the body starts to fall, a break rod disposed at the channel can be moved from an inactive position into an active position where it can stop the falling movement of the body. U.S. Pat. No. 3,545,749 describes a reaction time measuring method employing a rectangular card of markable material. One person manually releases the card which falls freely down a wall. A second person observes the first person's hand movement releasing the card and attempts to stop the card by pitting it against the wall. U.S. Pat. No. 3,717,347 describes an apparatus wherein an operator inserts a coin at the top of a column allowing the coin to fall down a channel. A breaking linkage is depressed by the operator to catch the coin falling as rapidly as possible. U.S. Pat. No. 3,747,589 describes a reaction time testing apparatus wherein a body is dropped by a first person allowing a second person to grasp the dropping body with their hand.

The above referenced U.S. patents all employ an apparatus for testing reflex and reaction times of people. None of the above references employ a card falling along a vertical axis within a housing to be grabbed by a pair of gripper fingers as in the present invention which will be fully disclosed in the description below. There is a continued need for new and innovative game apparatus for testing reflex and reaction times of people.

SUMMARY OF THE INVENTION

I have invented a new game apparatus for testing reflex and reaction times of people for use in amusement parks, arcades, and the like. My invention employs a housing vertically mounted to a base positioned on a planar surface. The housing defines a channel and a vertical axis of the game apparatus. The housing encloses a card shaft and a lifter shaft vertically mounted in the channel and parallel to the vertical axis of the game apparatus. A card has a vertical collar mounted to a back surface with a collar aperture formed therein for surrounding the card shaft thereby enabling the card to move vertically along the card shaft.

A lifter has a lifter collar with an aperture formed therein for surrounding the lifter shaft thereby enabling the lifter to move vertically along the lifter shaft. The lifter collar engages a bracket mounted to vertical collar of the card permitting the operator to set the card in an upper limit. A magnetic solenoid retains the card at the upper limit.

A game player using the game apparatus of the present invention engages a start button which begins a time sequence. When the time sequence has ended, the magnetic solenoid has become de-energized, thereby releasing the card. The game player attempts to grab the falling card at the earliest possible time. A plurality of prize lines located on a front surface of the card provides the prize that is awarded to the game player. The game player engages a pair of finger grabbers to grab the falling card. A securing means retains the card to the finger grabbers. The operator releases the finger grabbers from the card after the prize has been determined.

A electronic cheat system is provided to prohibit the game player from the grabbing the card before it has started its downwardly movement. The game apparatus will not allow the card to fall after a game player has cheated until a brief time period has expired. An owner or operator can set a number of allowable "cheats" before the game ends.

BRIEF DESCRIPTION OF THE DRAWINGS

The invention may be best understood by those having ordinary skill in the art by reference to the following detailed description when considered in conjunction with the accompanying drawings in which:

FIG. 7 is a partial right side elevational view showing the card in a lower limit;

FIG. 8 is a partial right side elevational view showing the card being set in an upper limit by a lifter engaging a first bracket;

FIG. 9 is a partial right side elevational view showing the card in an upper limit and the lifter in a relaxed state;

FIG. 10 is a front elevational view of the card employed in the present invention;

DETAILED DESCRIPTION OF THE INVENTION

Figure 1:
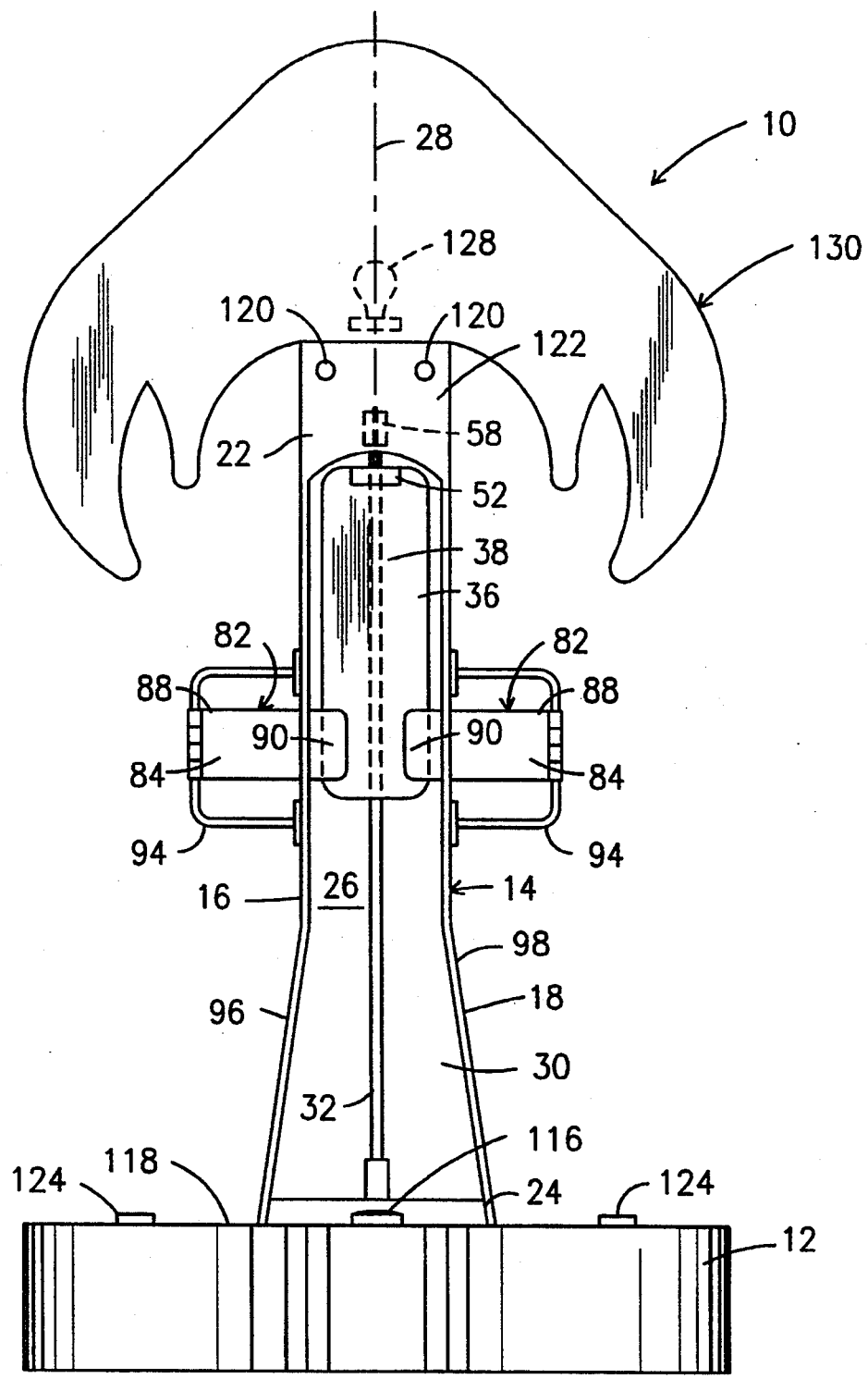
FIG. 1 is a front elevational view of a falling card game apparatus of the present invention.

Throughout the following detailed description, the same reference numerals refer to the same elements in all FIGURES.

Figure 2:
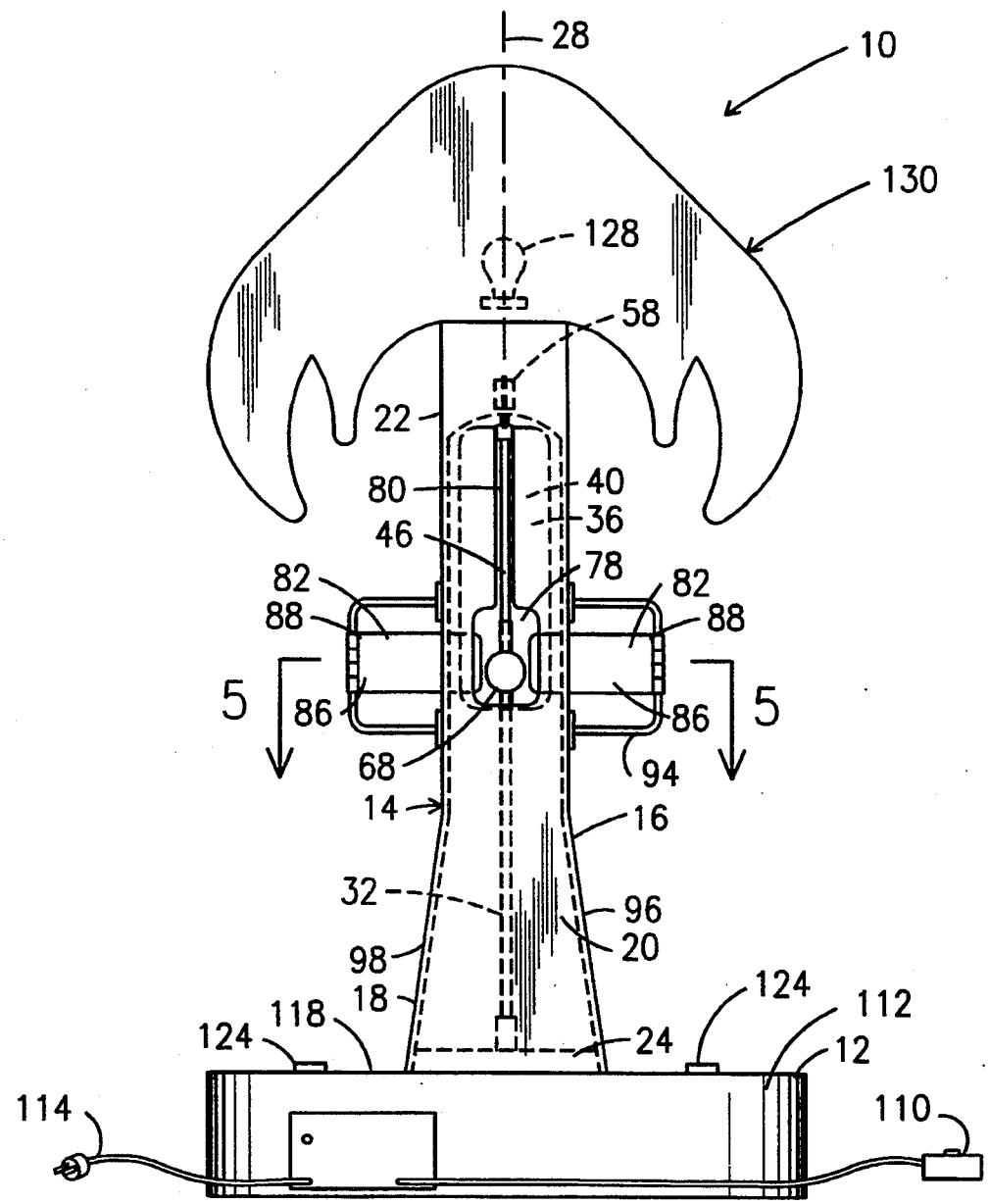
FIG. 2 is a back elevational view thereof.

Referring to FIGS. 1 and 2, a falling card game apparatus 10 is provided for testing the reflex and reaction times in people. Game apparatus 10 has a planar base 12 supporting a vertical housing 14. Housing 14 has opposed left and right side walls 16 and 18 respectively, a rear wall 20, and top and bottom ends 22 and 24 respectively. Left and right side walls 16 and 18 and rear wall 20 define a vertical channel 26. Housing 14 is vertically mounted to base 12 at bottom end 24 of housing 14. Housing 14 defines a vertical axis 28 of game apparatus 10. In the preferred embodiment, a translucent front panel 30 is provided enabling a game player (not shown) and operator (not shown) to view channel 26 defined within housing 14.

Figure 13:
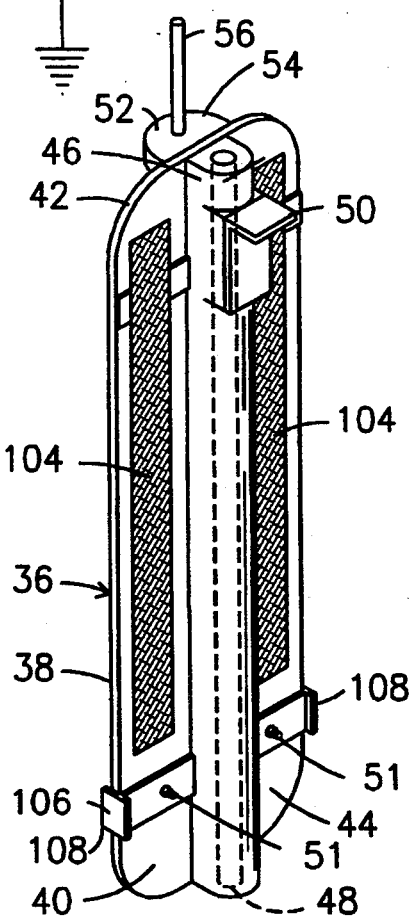
FIG. 13 is a perspective view of the card employed in the present invention.
Figure 14:
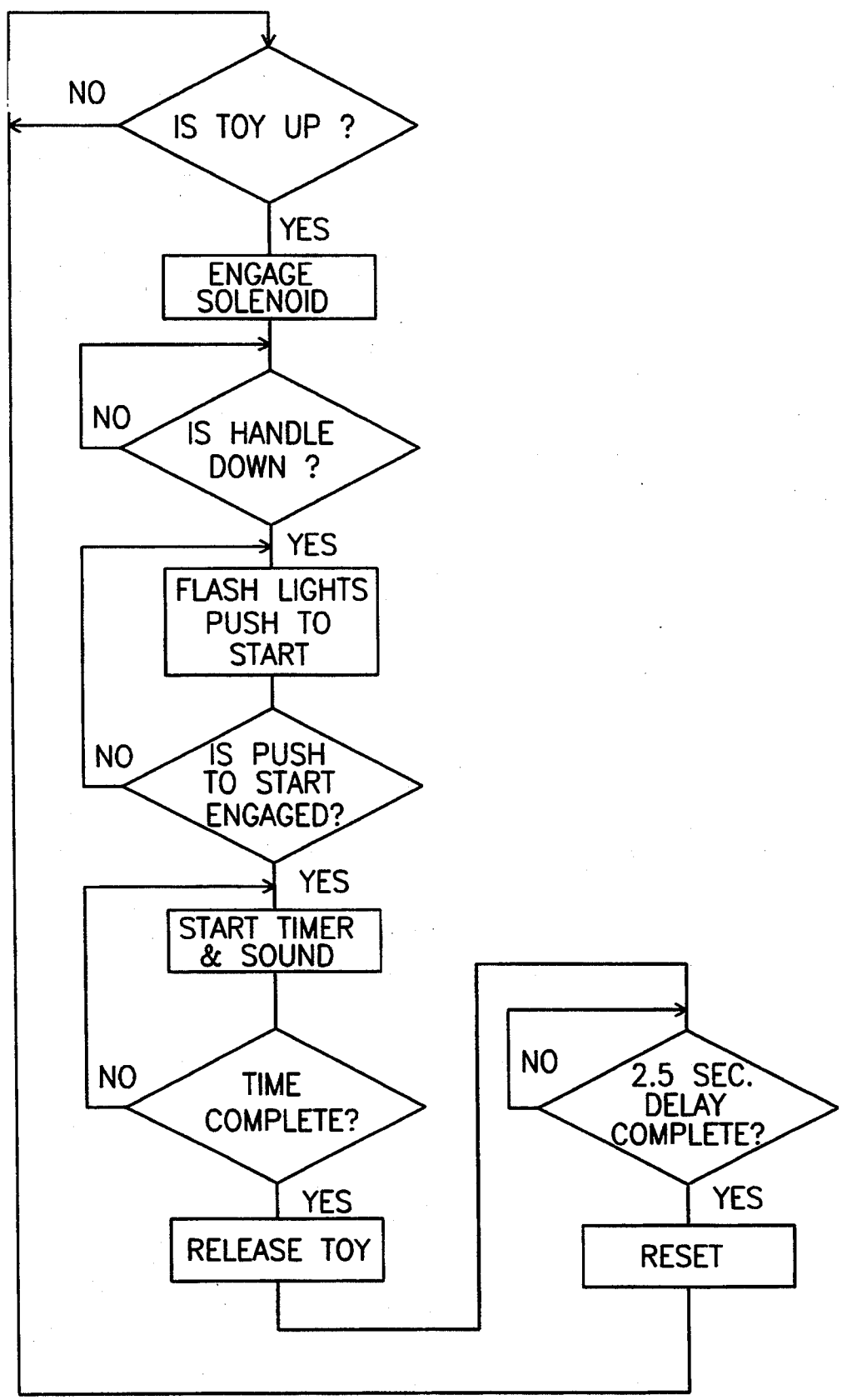
FIG. 14 is a logic diagram depicting the sequence of events that occur using the game apparatus of the present invention.

Referring to FIGS. 7, 8, and 9, a card shaft 32 is enclosed within channel 26 and vertically mounted to base 12 such that card shaft 32 is parallel to vertical axis 28. A lifter shaft 34 is enclosed and vertically mounted within channel 26 such that lifter shaft 34 is parallel to vertical axis 28 and intermediate card shaft 32 and rear wall 20 of housing 14. Referring to FIG. 13, a card 36 has opposed front and rear surfaces 38 and 40 respectively, top and bottom portions 42 and 44 respectively, and a vertical card collar 46 attached to rear surface 40 and having a collar aperture 48 formed therein. Collar aperture 48 surrounds card shaft 32 and enables card 36 to move vertically along card shaft 32.

Referring to FIGS. 7, 8, and 9, a first bracket 50 is attached to card collar 46 proximal to top portion 42 of card 36. A pin mounting block 52 having a top surface 54 is attached to front surface 38 of card 36 at top portion 42. A pin 56 is vertically mounted along top surface 54 of pin mounting block 52 such that pin 56 is parallel to card shaft 32 of game apparatus 10. A solenoid 58 having a bore 60 is mounted intermediate card shaft 32 and front panel 30 at top end 22 of housing 14. Bore 60 receives pin 56 when card 36 is set from a lower limit, as shown in FIG. 7, to an upper limit, as shown in FIG. 9. Bore 60 retains pin 56 as long as solenoid 58 is energized. When solenoid 58 is de-energized, bore 60 releases pin 56 thereby allowing card 36 to fall downwardly. In the preferred embodiment, a magnetic solenoid is employed in game apparatus 10 of the present invention.

Referring to FIGS. 7, 8, and 9, a lifter 62 having a bar 64, a lifter collar 66, and a handle 68 is provided for setting card 36 at the upper limit from the lower limit. Handle 68 is attached to a first end 70 of bar 64. Lifter collar 66 is attached perpendicularly in relation to bar 64 at a second end 72 of bar 64. Lifter collar 66 has a lifter aperture 74 formed therein for surrounding lifter shaft 34 thereby enabling vertical movement of lifter 62 along lifter shaft 34. Lifter collar 66 engages first bracket 50 for setting card 36 at the upper limit, as shown in FIG. 8. A stop 76 attached to rear wall 20 of housing 14 positions lifter 62 in a relaxed state thereby prohibiting any further downward movement of lifter 62 along lifter shaft 34.

Referring to FIG. 2, a rear wall opening 78 is formed in rear wall 20 of housing 14 to allow inspection of lifter 62 and rear surface 40 of card 36. Referring to FIGS. 7, 8, and 9, rear wall opening 78 further allows partial extension of lifter 62 from housing 14 in a direction opposite to translucent front panel 30. Referring to FIG. 2, a rear wall channel 80 formed in rear wall 20 of housing 14 extends upwardly from rear wall opening 78 enabling vertical movement of lifter 62.

Figure 5:
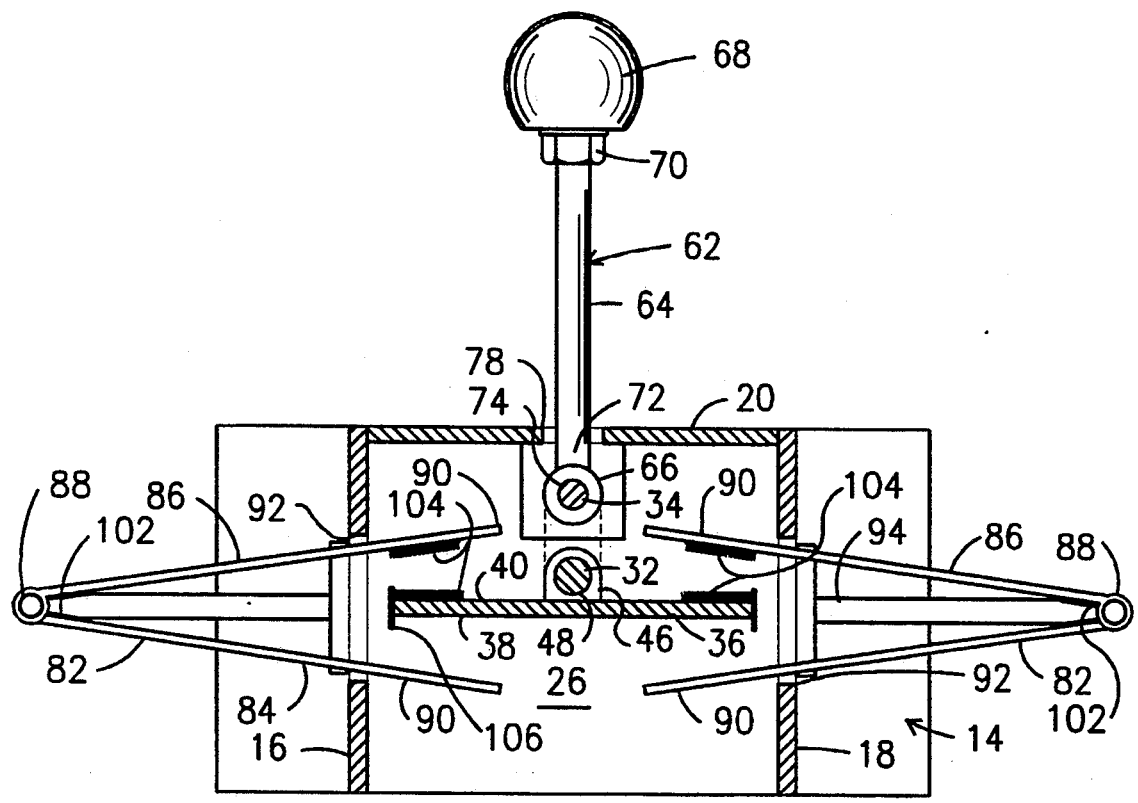
FIG. 5 is a cross sectional view along lines 5—5 of FIG. 2 showing a pair of opposed finger grabbers of the present invention in a relaxed state.
Figure 6:
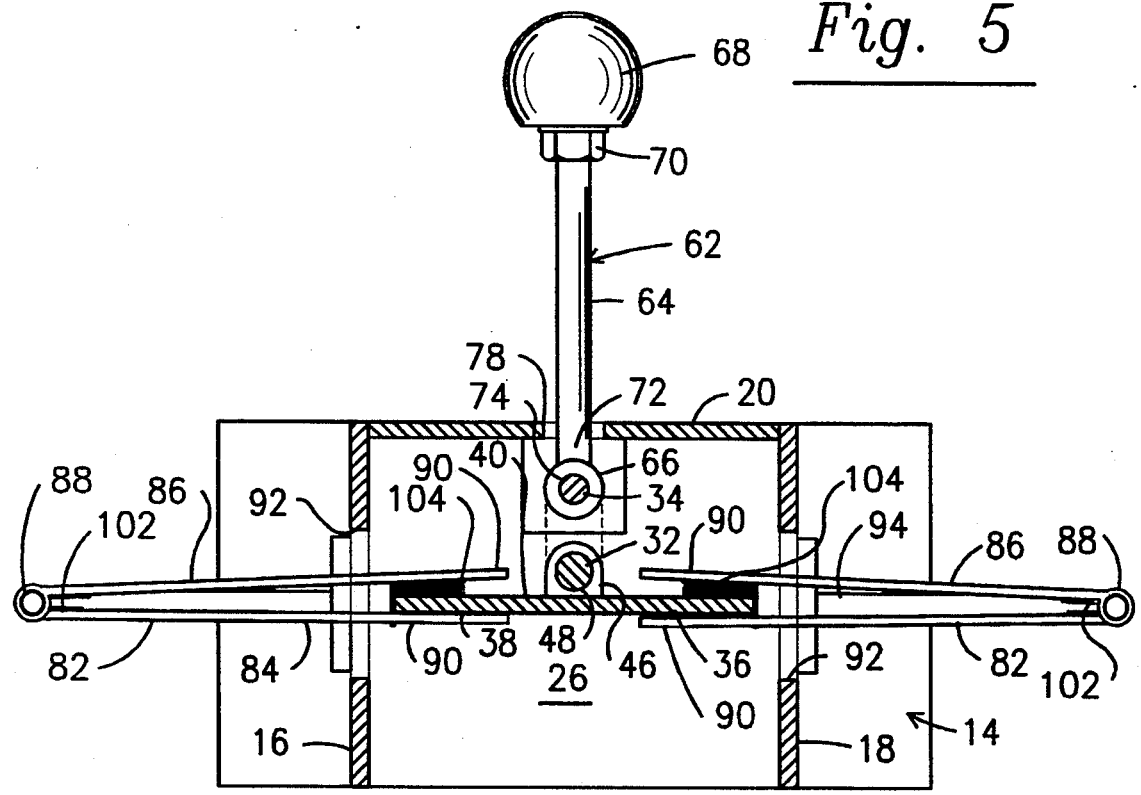
FIG. 6 is a cross sectional view along lines 5—5 of FIG. 2 showing the pair of opposed finger grabbers of the present invention in a compressed state engaging a card.
Figure 12:
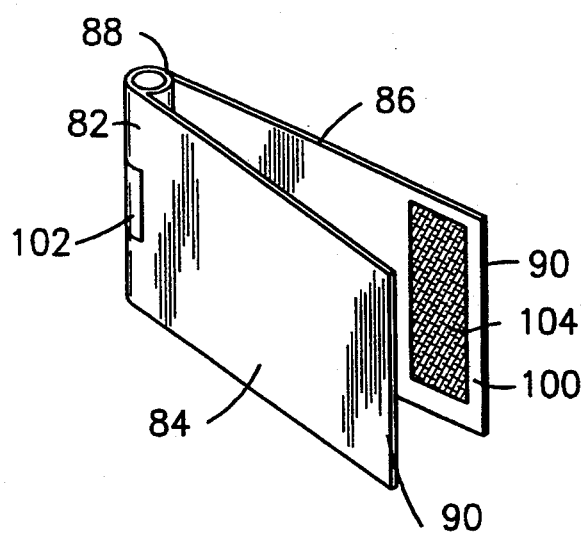
FIG. 12 is a perspective view of a finger grabber employed in the present invention.

Referring to FIGS. 5 and 6, a pair of opposed finger grabbers 82 have front and rear plates 84 and 86 respectively and first and second ends 88 and 90 respectively. Second ends 90 are inserted through a pair of opposed openings 92 formed in left and right side walls 16 and 18 of housing 14 for grabbing card 36. Referring to FIGS. 1 and 2, first ends 88 are fixably mounted to a pair of opposed support members 94 positioned on opposed outer surfaces 96 and 98 respectively of left and right side walls 16 and 18. As shown in FIG. 5, a distance between front and rear plates 84 and 86 gradually increases towards second ends 90 in relation to first ends 88 enabling second ends 90 to surround front and rear surfaces 38 and 40 of card 36 when finger grabbers 82 are in a relaxed state. As shown in FIG. 6, front and rear plates 84 and 86 grab card 36 to prohibit further downward movement of card 36. Referring to FIG. 12, rear plates 86 of finger grabbers 82 have a conductive inner surface 100 for use in a cheat circuit employed in game apparatus 10. In the preferred embodiment, conductive inner surface 100 is provided by polishing second end portion 90 of rear plate 86 of finger grabbers 82.

Referring to FIGS. 5 and 6, a spring 102 is inserted between front and rear plates 84 and 86 of finger grabbers 82 proximal to first ends 88 of finger grabbers 82. Spring 102 permits compression of front and rear plates 84 and 86 for grabbing card 36, as shown in FIG. 6, and permits return of front and rear plates 84 and 86 to a relaxed state, as shown in FIG. 5. Velcro 104 is attached to rear surface 40 of card 36 and to inner surfaces 100 of rear plates 86 of finger grabbers 82 proximal to second ends 90 of finger grabbers 82 for retaining card 36 at a position where a game player has grabbed card 36 with finger grabbers 82. Other like materials permitting finger grabbers 82 to retain card 36 at a fixed position can be employed in game apparatus 10. Referring to FIG. 10, front surface 38 of card 36 has a plurality of prize lines 37 for indicating a position where a game player has stopped the downward movement of card 36. A plurality of cards 36 having prize lines 37 indicated at various positions can be used with game apparatus 10 of the present invention.

Referring to FIG. 13, a second bracket 106 is mounted to rear surface 40 of card 36 at bottom portion 44. Second bracket 106 and first bracket 50 are mounted by a plurality of bolts 51. Second bracket 106 has a pair of tabs 108 positioned at opposed ends for engaging conductive inner surfaces 100 of rear plates 86 of finger grabbers 82 for completing a signal path in the cheat circuit. Tabs 108 extend perpendicularly from front and rear surfaces 38 and 40 of card 36 about ¼ inch.

Referring to FIG. 2, a foot switch 110 is provided along a back surface 112 of planar base 12 for engagement by a game operator to reset game apparatus 10 when a game player has completed a game. A power cord 114 is provided along back surface 112 of planar base 12 for providing electrical current to game apparatus 10. In the preferred embodiment, ac current is employed, as shown in FIG. 2, although a dc power source (not shown) can be employed with game apparatus 10 of the present invention.

Figure 3:
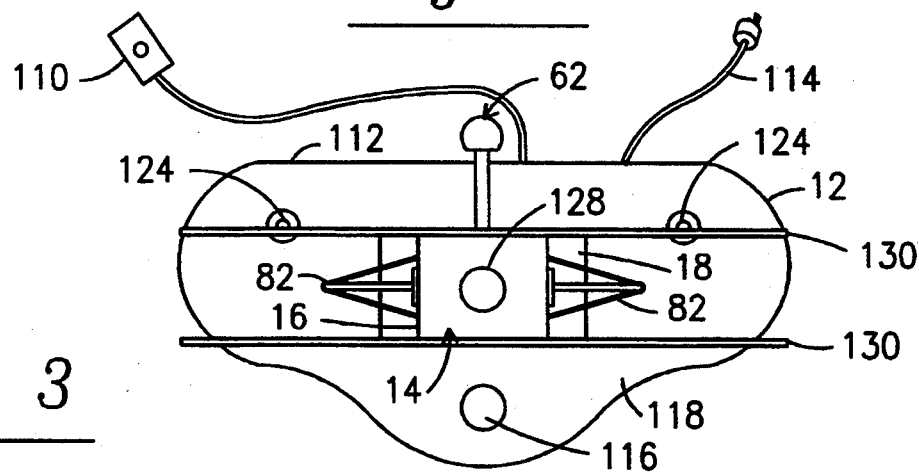
FIG. 3 is a top plan view thereof.
Figure 4:
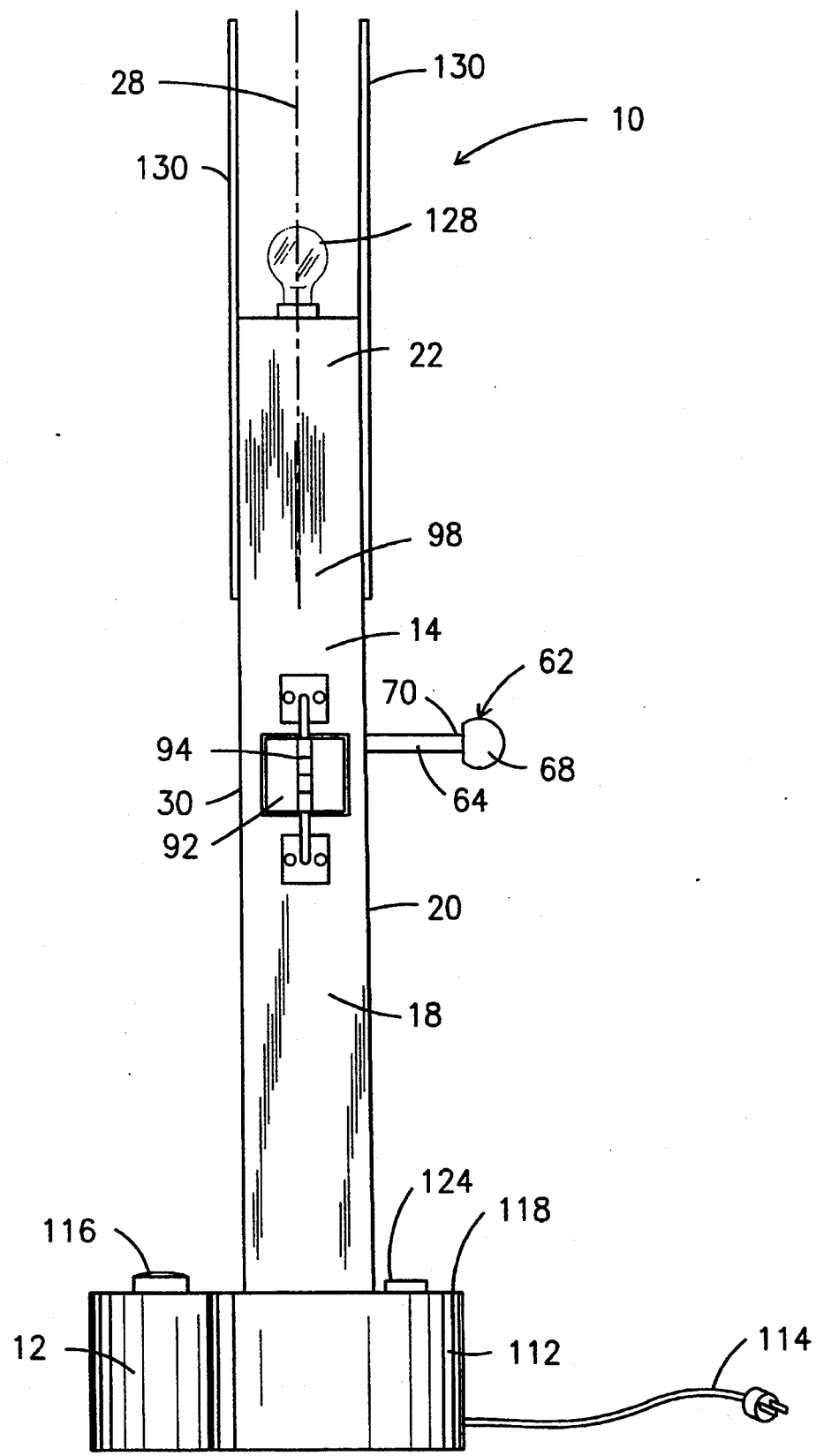
FIG. 4 is a right side elevational view thereof.
Figure 11:
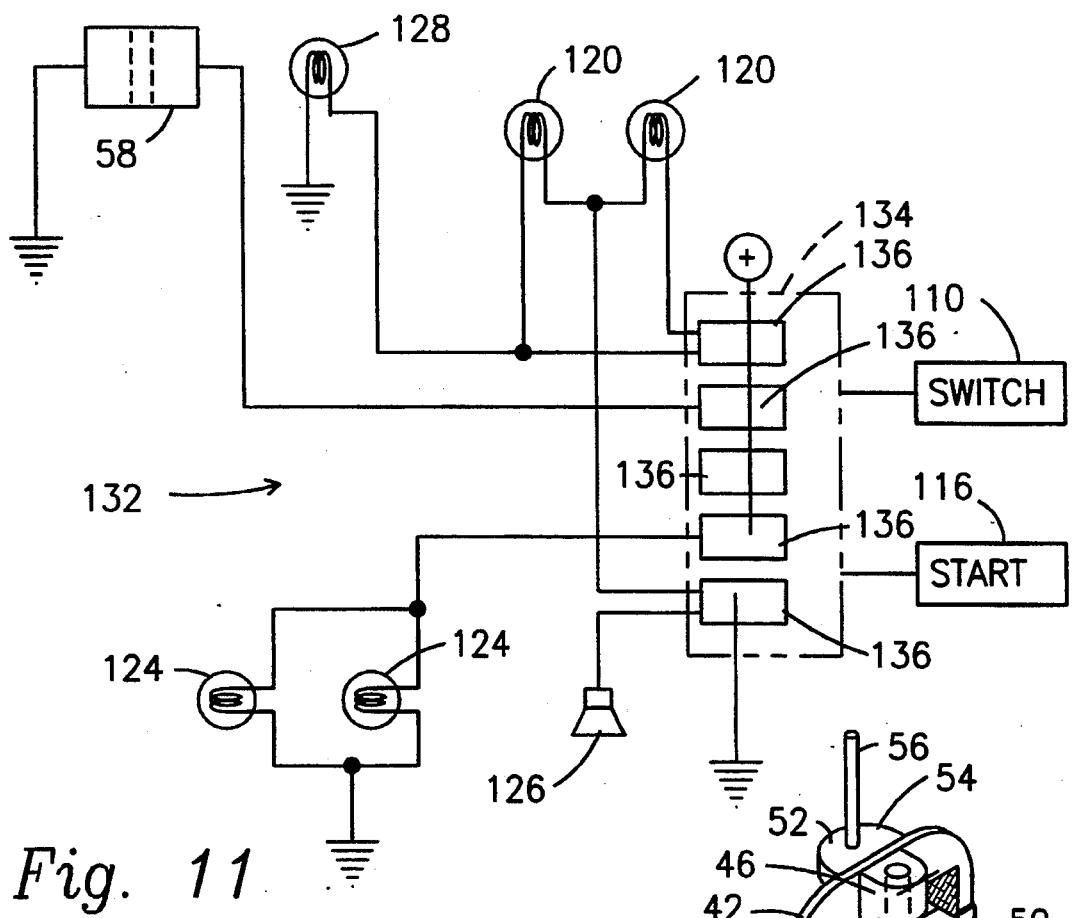
FIG. 11 is a circuit diagram showing the electrical components employed in the present invention.

Referring to FIG. 3, a start button 116 is provided along a top surface 118 of planar base 12 for engagement by a game player to initiate a time sequence, wherein at termination of the time sequence, the solenoid 58 is de-energized thereby releasing pin 56 from bore 60 which in turn allows card 36 to fall downward. In the preferred embodiment, start button 116 is illuminated by a light (not shown). Referring to FIG. 1, a pair of start sequence lights 120 are provided at top end 22 of housing 14 in a skirt portion 122, positioned directly above translucent front panel 30. Start sequence lights 120 alternatively illuminate as the time sequence is running. When the time sequence has terminated, start sequence lights 120 cease to alternatively illuminate, wherein one of the pair of sequence lights 120 remains illuminated. Referring to FIG. 11, a sound emitting device 126 produces a repeating tone wherein the interval between each tone diminishes as the time sequence approaches its termination. In the preferred embodiment, sound emitting device 126 is a piezo electric buzzer mounted within base 12. Game apparatus 10 contains 16 different time sequences which are randomly chosen by game apparatus 10 during each game to prohibit a game player from predicting when card 36 will begin its downward movement.

Referring to FIG. 3, a pair of cheat lights 124 are provided along top surface 118 in planar base 12 for alerting a game player and an operator that a cheat has occurred. A cheat occurs when a game player engages finger grabbers 82 against card 36 before card 36 has begun its downward movement. Tabs 108 engage conductive inner surface 100 on rear plate 86 of finger grabbers 82 thereby closing a circuit and allowing a signal flow to pass. Cheat lights 124 illuminate if a game player has engaged finger grabbers 82 against card 36 prior to the start sequence terminating. Referring to FIG. 1, a top light 128 is positioned above top end 22 of housing 14 to illuminate a top housing 130 mounted at top end 22 above housing 14. Top light 128 alternately flashes along with one of the pair of start sequence lights 120 and remains illuminated with the one start sequence light 120 that remains illuminated after the time sequence has terminated. After a game player has completed a game, an operator engages switch 110, thereby energizing solenoid 58 and providing electrical current to start sequence lights 120, top light 128, and the light (not shown) in start button 116.

Referring to FIG. 11, an electronic circuit 132 is used in game apparatus 10 for providing signal paths between solenoid 58, switch 110, start button 116, start sequence lights 120, cheat lights 124, sound emitting device 126, top light 128, and a circuit control means 134 for controlling electronic circuit 132. In the preferred embodiment, circuit control means 134 is a controller card having a plurality of relays 136. Relays 136 provide outputs for solenoid 58, start sequence lights 120, cheat lights 124, top light 128, and game apparatus 10. Circuit control means 134 further contains software enabling the operator or owner to manipulate start sequence times and to provide an allowable number of cheats performed by a game player before a game is considered over. In the preferred embodiment, a game player is allowed to cheat three times whereafter the game is terminated. The software randomly chooses one of the sixteen time sequences to prohibit a game player from memorizing a pattern of the time sequences thereby anticipating the downwardly movement of card 36.

Referring to FIG. 13, a logic diagram is provided to indicate the sequence of events which occur during a single game using game apparatus 10. First, game apparatus 10 is provided with electronic current by power cord 114. Next, switch 110 is engaged, closing a signal path, thereby energizing solenoid 58. Lifter 62 is engaged upwardly moving card 36 to its upward limit. Solenoid 58 holds card 36 and lifter 62 is placed in its relaxed state against stop 76. Start button 116 is engaged by a game player. A time sequence is chosen by the software and begins to count. Start sequence lights 120 and top light 128 begin to flash and sound emitting device 126 produces a repeating tone. Time sequence terminates thereby opening a signal path, thereby de-energizing solenoid 58. Card 36 is released from solenoid 58, begins downward movement, wherein a game player attempts to grab card 36 with finger grabbers 82. A final time delay is provided after card 36 has stopped its downward momentum, to determine if card 36 has been grabbed which would provide a win to a game player. In the preferred embodiment, the final time delay is 2.5 seconds. The final time delay can be manipulated through the software by the operator or owner. A cheat detection system is inserted within the sequence of events of game apparatus 10. If a cheat has occurred, the signal path to solenoid 58 will remained closed, thereby enabling solenoid 58 to remain energized keeping card 36 from initiating any downward movement. A short time delay will pass before another time sequence begins to count.

In an alternate embodiment (not shown), game apparatus 10 has a coin slot, a ticket dispenser, a drive means, and a prize detection circuit. The coin slot enables game apparatus 10 to be employed in a arcade, wherein an operator of game apparatus 10 would not be necessary. A game player inserts proper coinage in the coin slot thereby starting a game. A drive means sets card 36 in solenoid 58. Start button 116 is engaged by the player initiating the time sequence. The card drops at the termination of the time sequence wherein the player attempts to grab card 36 with finger grabbers 82 before card 36 has reached a downward limit. If the game player has successfully grabbed card 36, a prized detection circuit would indicate which prize should be awarded. The ticket dispenser would produce a ticket for the game player to remit for a his or her prize at an alternate location. The alternate embodiment of game apparatus 10 incorporates all other components of the preferred embodiment set forth in the above description.

Equivalent elements can be substituted for the elements employed in this invention to obtain the same results in the same way.

Having thus described the invention what is claimed and desired to be secured by Letters Patent is:

1. A falling card game apparatus for testing the reflex and reaction times of people, the game apparatus comprising,
   a base,
   a housing having opposed left and right side walls, a rear portion, and top and bottom ends defining a channel, the housing vertically mounted to the base at the bottom end and defining a vertical axis of the game apparatus,
   a shaft enclosed within the channel and mounted to the base such that the shaft is parallel to the vertical axis,
   a card having opposed front and rear surfaces, top and bottom portions, and a collar portion positioned along the rear surface, the collar portion having an aperture formed therein for surrounding the shaft, the card moveable along the shaft, a solenoid having a bore formed therein and mounted at the top end of the housing for retaining the card at an upper limit when the solenoid is energized, the bore receiving a pin positioned on a mounting block attached to the front surface of the card proximal to the top portion of the card, the pin parallel to the vertical axis of the game apparatus, a pair of opposed resilient finger grabbers having front and rear plates and first and second ends, the finger grabbers partially inserted through opposed openings in the left and right side walls of the housing, the second ends of the finger grabbers positioned to stop downward momentum of the card along the shaft, the first ends of the finger grabbers mounted to support members located outside the opposed openings formed in the left and right side walls of the housing, means for lifting the card upwardly to the upper limit, means for supplying electrical current to the game apparatus, means for energizing the solenoid, and means for de-energizing the solenoid.

2. The falling card game apparatus according to claim 1, further comprising means for controlling an electronic circuit, the electronic circuit for providing signal paths between the solenoid, means for energizing the solenoid, means for de-energizing the solenoid, and means for controlling the electronic circuit.

3. The falling card game apparatus according to claim 2, wherein the means for controlling an electronic circuit is a controller card having a plurality of relays.

4. The falling card game apparatus according to claim 2, wherein the means for supplying electrical current to the game is a power cord attached through the base and connected to a power source.

5. The falling card game apparatus according to claim 4, wherein the power source is alternating current.

6. The falling card game apparatus according to claim 4, wherein the power source is direct current.

7. The falling card game apparatus according to claim 2, wherein the means for energizing the solenoid is a switch attached through the base, the switch completing a signal path which provides electrical current to the solenoid.

8. The falling card game apparatus according to claim 2, wherein the means for de-energizing the solenoid is a button positioned along a top surface of the base, the button opening a signal path which provides electrical current to the solenoid.

9. The falling card game apparatus according to claim 1, wherein the means for lifting the card upwardly to the upper limit is an rearwardly extending portion positioned along the rear surface of the card, the rearwardly extending portion engageable from the rear portion of the housing.

10. The falling card game apparatus according to claim 1, wherein the solenoid is a magnetic solenoid.

11. A falling card game apparatus for testing the reflex and reaction times of people, the game apparatus comprising, a base, a housing having opposed left and right side walls, a rear wall, and top and bottom ends, the left and right side walls and rear wall defining a vertical channel, the rear wall having a rear wall opening and upwardly extending channel formed therein, the housing vertically mounted at the bottom end to the base, the housing defining a vertical axis of the game apparatus, a first shaft enclosed within the channel and vertically mounted to the base, a card having opposed front and rear surfaces, top and bottom portions, and a vertical card collar positioned along the rear surface, the card collar having a collar aperture formed therein for surrounding the first shaft and enabling vertical movement of the card along the first shaft, an rearwardly extending portion positioned along the card collar proximal to the top portion of the card, a second shaft enclosed within the channel and vertically mounted to a stop such that the second shaft is intermediate the first shaft and the rear wall of the housing, the stop attached to the rear wall of the housing, a lifter member moveable along the second shaft and engageable with the first bracket for setting the card at an upper limit, a solenoid mounted at the top end of the housing for retaining the card at the upper limit when the solenoid is energized, the solenoid having a bore for receiving a pin mounted along a top surface of a pin mounting block, the pin parallel to the vertical axis of the game apparatus, the pin mounting block attached to the front surface of the card proximal to the top portion of the card, the solenoid releasing the pin from the bore when the solenoid is de-energized, a pair of opposed resilient finger grabbers having front and rear plates and first and second ends, the second ends of the finger grabbers inserted through opposed openings formed in the left and right side walls of the housing for grabbing the card, the first ends of the finger grabbers mounted to support members such that a distance between the front and rear plates gradually increases towards the second ends in relation to the first ends enabling the second ends to surround the front and rear surfaces of the card when the finger grabbers are in a relaxed state, the support members positioned outside the housing proximal to the openings formed in the left and right side walls of the housing, means for supplying electrical current to the game apparatus, means for energizing the solenoid, and means for de-energizing the solenoid.

12. The falling card game apparatus according to claim 11 further comprising, means for controlling an electronic circuit, the electronic circuit for providing signal paths between the solenoid, means for energizing the solenoid, means for de-energizing the solenoid, and means for controlling the electronic circuit, and a second bracket attached to the rear surface of the card at the bottom portion of the card, the second bracket having a pair of front and rearwardly extending opposed tabs engaging a conductive inner surface of the rear plates of the finger grabbers for completing a cheat signal path in the electronic circuit.

13. The falling card game apparatus according to claim 12, wherein the means for supplying electrical current to the game is a power cord attached through the base and connected to a power source.

14. The falling card game apparatus according to claim 13, wherein the power source is alternating current.

15. The falling card game apparatus according to claim 13, wherein the power source is direct current.

16. The falling card game apparatus according to claim 12, wherein the means for energizing the solenoid is a switch attached through the base, the switch completing a signal path which provides electrical current to the solenoid.

17. The falling card game apparatus according to claim 12, wherein the means for de-energizing the solenoid is a button positioned along a top surface of the base, the button opening a signal path which provides electrical current to the solenoid.

18. A falling card game apparatus for testing the reflex and reaction times of people, the game apparatus comprising, a planar base, a housing having opposed left and right side walls, a rear wall, and top and bottom ends, the left and right side walls and rear wall defining a vertical channel, the rear wall having a rear wall opening and upwardly extending channel formed therein, the housing vertically mounted at the bottom end to the base, the housing defining a vertical axis of the game apparatus, a card shaft enclosed within the channel and vertically mounted to the base, a lifter shaft enclosed within the channel and vertically mounted to a stop such that the lifter shaft is intermediate the card shaft and rear wall of the housing, the stop mounted to the rear wall of the housing a card having opposed front and rear surfaces, top and bottom portions, and a vertical card collar attached to the rear surface, the card collar having a collar aperture formed therein for surrounding the card shaft and enabling vertical movement of the card along the card shaft, a first bracket attached to the card collar proximal to the top portion of the card, a lifter having a bar, a handle, and a lifter collar, the handle mounted at a first end of the bar and the lifter collar mounted perpendicularly in relation to the bar at a second end of the bar, the lifter collar having a lifter aperture formed therein for surrounding the lifter shaft and enabling vertical movement of the lifter along the lifter shaft, the lifter collar engageable with the first bracket for setting the card at an upper limit, a magnetic solenoid mounted at the top end of the housing for retaining the card at the upper limit when the solenoid is energized, the solenoid having a bore for receiving a pin mounted along a top surface of a pin mounting block, the pin parallel to the vertical axis of the game apparatus, the pin mounting block attached to the front surface of the card at the top portion of the card, the solenoid releasing the pin from the bore when the solenoid is de-energized, a pair of opposed finger grabbers having front and rear plates and first and second ends, the second ends of the finger grabbers inserted through opposed openings formed in the left and right side walls of the housing for grabbing the card, the first ends of the finger grabbers fixably mounted to support members such that a distance between the front and rear plates gradually increases towards the second ends in relation to the first ends enabling the second ends to surround the front and rear surfaces of the card when the finger grabbers are in a relaxed state, the support members positioned outside the housing proximal to the openings formed in the left and right side walls of the housing, a spring inserted intermediate the front and rear plates of the pair of finger grabbers for permitting compression of the front and rear plates for grabbing the card and for permitting return of the finger grabbers back to a relaxed state after the finger grabbers have released the card, a power cord attached through the base and connected to a power source, a switch attached through the base for completing a signal path which provides electrical current to the solenoid, a button positioned along a top surface of the base, the button opening the signal path which provides electrical current to the solenoid, a controller card having a plurality of relays for controlling a plurality of outputs, an electronic circuit for providing signal paths between the solenoid, switch, button, and controller card, and a second bracket attached to the rear surface of the card at the bottom portion of the card, the second bracket having a pair of front and rearwardly extending opposed tabs engaging a conductive inner surface of the rear plates of the finger grabbers for completing a cheat signal path in the electronic circuit.

19. The falling card game apparatus according to claim 18 further comprising, a top light mounted above the top end of the housing for illuminating a top housing, a pair of start sequence lights mounted in a skirt portion of the top end of the housing for indicating that the game apparatus has begun a game, a pair of cheat lights positioned along the top surface of the base for providing a visual indicator that the cheat signal path has been completed, a sound emitting device for providing a repeating tone during a start sequence, a translucent front panel positioned in front of the channel and parallel to the rear wall of the housing, and means for retaining the card at a position where a game player has grabbed the card with the finger grabbers attached to the inner surfaces of the rear plates of the finger grabbers and to the rear surface of the card.

* * * * *